(12) United States Patent
Hagihara et al.

(10) Patent No.: US 6,670,360 B2
(45) Date of Patent: Dec. 30, 2003

(54) OPTICALLY ACTIVE PYRROLOPYRIDAZINE DERIVATIVES

(75) Inventors: Masahiko Hagihara, Ube (JP); Nobuhiko Shibakawa, Ube (JP); Keiji Matsunobu, Ube (JP); Hiroshi Fujiwara, Ube (JP); Keiichi Ito, Kawaguchi (JP)

(73) Assignees: Sankyo Company, Limited, Tokyo (JP); Ube Industries, Ltd., Ube (JP)

( * ) Notice: Subject to any disclaimer, the term of this patent is extended or adjusted under 35 U.S.C. 154(b) by 223 days.

(21) Appl. No.: 10/021,214

(22) Filed: Dec. 12, 2001

(65) Prior Publication Data

US 2002/0156079 A1 Oct. 24, 2002

Related U.S. Application Data

(63) Continuation of application No. PCT/JP00/03895, filed on Jun. 15, 2000.

(30) Foreign Application Priority Data

Jun. 15, 1999 (JP) .............................................. 11-167679

(51) Int. Cl.⁷ ..................... C07D 487/04; A61K 31/50
(52) U.S. Cl. ....................................... 514/248; 544/236
(58) Field of Search ........................... 514/248; 544/236

(56) References Cited

U.S. PATENT DOCUMENTS 5,534,515 A 7/1996 Grundler et al.
6,063,782 A 5/2000 Kimura et al.

FOREIGN PATENT DOCUMENTS

| EP | 742218 A1 | 11/1996 |
| WO | WO 91/17164 A1 | 11/1991 |
| WO | WO 92/06979 A1 | 4/1992 |
| WO | 93/08190 | 4/1993 |

*Primary Examiner*—John M. Ford
(74) *Attorney, Agent, or Firm*—Frishauf, Holtz, Goodman & Chick, P.C.

(57) ABSTRACT

An optically active pyrrolopyridazine compound of the formula (I) or a pharmaceutically acceptable salt thereof:

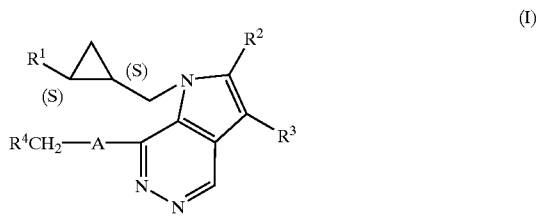

wherein $R^1$ is alkyl; $R^2$ and $R^3$ are each independently alkyl; $R^4$ is optionally substituted aryl; and A is imino, oxygen or sulfur. The pyrrolopyridazine compound or pharmaceutically acceptable salts thereof of the present invention exhibit excellent gastric acid secretory inhibition activity and gastric mucous membrane protection activity, as well as excellent antibacterial activity against *Helicobacter pylori*. They are useful medicines and are particularly useful for treating or preventing ulcerative diseases.

27 Claims, No Drawings

OPTICALLY ACTIVE PYRROLOPYRIDAZINE DERIVATIVES

This application is a continuation application of International Application PCT/JP00/03895 filed Jun. 15, 2000, which was not published in English under PCT Article 21(2).

BACKGROUND OF THE INVENTION

1. Field of the Invention

This invention relates to optically active pyrrolopyridazine derivatives of formula (I) or pharmaceutically acceptable salts thereof.

This invention further relates to pharmaceutical compositions comprising an optically active pyrrolopyridazine derivative of formula (I) or a pharmaceutically acceptable salt thereof (preferably compositions for prevention or treatment of an ulcerative disease) as an active ingredient.

In another aspect, this invention relates to the use of an optically active pyrrolopyridazine derivative of formula (I) or a pharmaceutically acceptable salt thereof in the preparation of a pharmaceutical composition (preferably a composition for the prevention or treatment of an ulcerative disease).

In another aspect, this invention relates to a method for the prevention or treatment of disease (preferably an ulcerative disease), which method comprises administering a pharmaceutically effective amount of an optically active pyrrolopyridazine derivative of formula (I) or a pharmaceutically acceptable salt thereof to a warm-blooded animal (preferably a human) in need of such treatment.

In yet another aspect, this invention relates to a process for the preparation of optically active pyrrolopyridazine derivatives of formula (I) and pharmaceutically acceptable salts thereof.

2. Background Information

It has been considered that an imbalance between aggressive factors and protective factors against the gastric mucous membrane induces a peptic ulcer. Gastric acid secretion is an aggressive factor and suppression of gastric acid secretion is useful in the prevention and treatment of the disease. Anticholinergic drugs, histamine H2 receptor antagonists such as cimetidine and proton-pump inhibitors such as omeprazole have been clinically used as a gastric acid secretory inhibitor. Although these drugs are excellent therapeutic agents for ulcerative disease, the disease may recur after cessation of the therapy. It has been recently reported that *Helicobacter pylori* relates to the recurrence of the ulcerative disease. Actually there have been some attempts to use a gastric acid secretory inhibitor in combination with an antibacterial ag for treatment of the disease.

Accordingly a compound that exhibits potent gastric acid secretory inhibition activity, excellent gastric mucous membrane protection activity and potent antibacterial activity against *Helicobacter pylori* would be expected to be an excellent prophylactic and therapeutic agent for gastric ulcer disease.

Some pyrrolopyridazine derivatives that have gastric acid secretory inhibition activity and protect gastric mucous membranes have been described in U.S. Pat. No. 6,063,782, WO 91/17164, WO 92/06979 and WO 93/08190. In Japanese Patent Application Publication Hei 7-247285 the activity against *Helicobacter pylori* of some pyrrolopyridazine derivatives has also been described.

SUMMARY OF THE INVENTION

The inventors have continued an investigation on the pharmacological activities of pyrrolopyridazine derivatives in order to discover compounds that exhibit potent gastric acid secretory inhibition activity, protect gastric mucous membranes and have excellent antibacterial activity against *Helicobacter pylori* for a long time. It was proved that some optically active pyrrolopyridazine derivatives substituted with a trans-alkylcyclopropylmethyl group have such activities and are superior to the corresponding racemate as a medicament.

This invention relates to optically active pyrrolopyridazine derivatives of formula (I) hereinbelow or pharmaceutically acceptable salts thereof.

This invention further relates to pharmaceutical compositions comprising an optically active pyrrolopyridazine derivative of formula (I) or a pharmaceutically acceptable salt thereof (preferably compositions for prevention or treatment of ulcerative disease) as an active ingredient.

In another aspect, this invention relates to the use of an optically active pyrrolopyridazine derivative of formula (I) or a pharmaceutically acceptable salt thereof in the preparation of a pharmaceutical composition (preferably a composition for the prevention or treatment of ulcerative disease).

In another aspect, this invention relates to a method for the prevention or treatment of a disease (preferably an ulcerative disease), which method comprises administering a pharmaceutically effective amount of an optically active pyrrolopyridazine derivative of formula (I) or a pharmaceutically acceptable salt thereof to a warm-blooded animal (preferably a human) in need of such treatment.

In yet another aspect, this invention relates to a process for the preparation of optically active pyrrolopyridazine derivatives of formula (I) and pharmaceutically acceptable salts thereof.

An optically active pyrrolopyridazine derivative of the present invention has the following formula:

(I)

[Chemical structure of pyrrolopyridazine derivative with $R^1$, $R^2$, $R^3$, $R^4CH_2$—A— substituents and (S),(S) stereochemistry]

wherein:

$R^1$ is a $C_1$–$C_6$ alkyl group;

$R^2$ and $R^3$ are each independently a $C_1$–$C_6$ alkyl group;

$R^4$ is a $C_6$–$C_{10}$ aryl group which is optionally substituted with one or more substituents selected from the group consisting of $C_1$–$C_6$ alkyl, halogeno $C_1$–$C_6$ alkyl, $C_1$–$C_6$ alkoxy, halogeno $C_1$–$C_6$ alkoxy and halogen; and A is an imino group, an oxygen atom or a sulfur atom.

DETAILED DESCRIPTION OF THE INVENTION

The $C_1$–$C_6$ alkyl moiety of the alkyl group in the definitions of $R^1$, $R^2$, $R^3$ and $R^4$ and of the halogeno $C_1$–$C_6$ alkyl, $C_1$–$C_6$ alkoxy and halogeno $C_1$–$C_6$ alkoxy group included in the definition of $R^4$ is, for example, a methyl, ethyl, propyl, isopropyl, butyl, isobutyl, s-butyl, t-butyl, pentyl or hexyl group; is preferably a $C_1$–$C_4$ alkyl group; more preferably a methyl or ethyl group and most preferably methyl.

The halogen atom included in the definition of $R^4$ is, for example, a fluorine, chlorine, bromine or iodine atom; preferably a fluorine, chlorine or bromine atom and more preferably a fluorine or chlorine atom.

The $C_6$–$C_{10}$ aryl group in the definition of $R^4$ is, for example, a phenyl or naphthyl group; preferably a phenyl group. The number of substituents on the aryl group is from 1 to 5; 1 to 3 is preferable, 1 or 2 is more preferable and 1 is the most preferable. The $C_6$–$C_{10}$ aryl group is optionally substituted with one or more substituents selected from the group consisting of $C_1$–$C_6$ alkyl, halogeno $C_1$–$C_6$ alkyl, $C_1$–$C_6$ alkoxy, halogeno $C_1$–$C_6$ alkoxy and halogen is preferably, for example, a phenyl, methylphenyl, (trifluoromethyl)phenyl, methoxyphenyl, (trifluoromethoxy)phenyl, (difluoromethoxy)phenyl, fluorophenyl, chlorophenyl, bromophenyl, difluorophenyl, chlorofluorophenyl, dichlorophenyl, trifluorophenyl, trichlorophenyl, naphthyl, methylnaphthyl, methoxynaphthyl, fluoronaphthyl, chloronaphthyl or bromonaphthyl group; more preferably a phenyl, 4-methylphenyl, 4-(trifluoromethyl)phenyl, 4-methoxyphenyl, 4-(trifluoromethoxy)phenyl, 4-(difluoromethoxy)phenyl, 2-, 3- or 4-fluorophenyl, 2-, 3- or 4-chlorophenyl, 4-bromophenyl, 2,4- or 2,6-difluorophenyl, 4-chloro-2-fluorophenyl, 2-chloro-4-fluorophenyl, 2,4- or 2,6-dichlorophenyl, 2,4,6-trifluorophenyl or 2,4,6-trichlorophenyl group; more preferably a 4-fluorophenyl, 4-chlorophenyl, 2,4-difluorophenyl, 4-chloro-2-fluorophenyl, 2-chloro-4-fluorophenyl or 2,4-dichlorophenyl group; most preferably a 4-fluorophenyl or 4-chlorophenyl group.

A is preferably an oxygen or sulfur atom, more preferably an oxygen atom.

The pharmaceutically acceptable salt of the compound of formula (I) is an acid addition salt, for example, a hydrohalogenic acid salt such as hydrofluoride, hydrochloride, hydrobromide and hydroiodide; a nitrate; a perchlorate; a sulfate; a phosphate; a carbonate; a $C_1$–$C_6$ alkylsulfonate which is optionally substituted with fluorine atom(s), such as methanesulfonate, trifluoromethanesulfonate, ethanesulfonate, pentafluoroethanesulfonate, propanesulfonate, butanesulfonate, pentanesulfonate and hexanesulfonate; a $C_6$–$C_{10}$ arylsulfonate such as benzenesulfonate and p-toluenesulfonate; a carboxylate, such as acetate, propionate, butyrate, benzoate, fumarate, maleate, succinate, citrate, tartrate, oxalate and malonate; or an amino acid salt such as glutamate and aspartate; preferably a hydrochloride, sulfate or carboxylate; more preferably a hydrochloride.

The compound of formula (I) of the present invention or a salt thereof can exist as a hydrate form and the scope of the present invention encompasses the hydrate form.

Preferred compounds of formula (I) of the present invention include:

(1) a compound wherein $R^1$ is a $C_1$–$C_4$ alkyl group;
(2) preferably a compound wherein $R^1$ is a methyl group;
(3) a compound wherein $R^2$ and $R^3$ are each independently a $C_1$–$C_4$ alkyl group;
(4) preferably a compound wherein $R^2$ and $R^3$ are each methyl groups;
(5) a compound wherein $R^4$ is a phenyl group substituted with 1 to 3 substituents selected from the group consisting of $C_1$–$C_4$ alkyl, halogeno $C_1$–$C_4$ alkyl, $C_1$–$C_4$ alkoxy, halogeno $C_1$–$C_4$ alkoxy, fluoro, chloro and bromo;
(6) preferably a compound wherein $R^4$ is a phenyl group substituted with 1 to 3 substituents selected from the group consisting of methyl, trifluoromethyl, methoxy, trifluoromethoxy, difluoromethoxy, fluoro, chloro and bromo;
(7) more preferably a compound wherein $R^4$ is a phenyl group substituted at the 2-, 4- and/or 6-positions with 1 or 2 substituents selected from the group consisting of fluoro and chloro,
(8) most preferably a compound wherein $R^4$ is a phenyl group substituted at the 4-position with a substituent selected from fluoro or chloro or a phenyl group substituted at the 2- and 4-positions with two substituents selected from the group consisting of fluoro and chloro;
(9) a compound wherein A is an oxygen atom or a sulfur atom; and/or
(10) more preferably compound wherein A is an oxygen atom.

Preferred compounds of formula (I) also include compounds wherein $R^1$ is selected from the group consisting of (1) and (2), $R^2$ and $R^3$ are selected from the group consisting of (3) and (4), $R^4$ is selected from the group consisting of (5), (6), (7) and (8) and A is selected from the group consisting of (9) and (10).

Such compounds include, for example,

(11) a compound wherein $R^1$ is a $C_1$–$C_4$ alkyl group, $R^2$ and $R^3$ are each independently $C_1$–$C_4$ alkyl groups, $R^4$ is a phenyl group substituted with 1 to 3 substituents selected from the group consisting of $C_1$–$C_4$ alkyl, halogeno $C_1$–$C_4$ alkyl, $C_1$–$C_4$ alkoxy, halogeno $C_1$–$C_4$ alkoxy, fluoro, chloro and bromo, and A is an oxygen atom or a sulfur atom;
(12) preferably a compound wherein $R^1$ is a methyl group, $R^2$ and $R^3$ are each methyl groups, $R^4$ is a phenyl group substituted with 1 to 3 substituents selected from the group consisting of methyl, trifluoromethyl, methoxy, trifluoromethoxy, difluoromethoxy, fluoro, chloro and bromo, and A is an oxygen atom or a sulfur atom;
(13) more preferably a compound wherein $R^1$ is a methyl group, $R^2$ and $R^3$ are each methyl groups, $R^4$ is a phenyl group substituted at the 2-, 4- and/or 6-positions with 1 or 2 substituents selected from the group consisting of fluoro and chloro, and A is an oxygen atom; and
(14) most preferably a compound wherein $R^1$ is a methyl group, $R^2$ and $R^3$ are each methyl groups, $R^4$ is a phenyl group substituted at the 4-position with a substituent selected from fluoro or chloro or a phenyl group substituted at the 2- and 4-positions with two substituents selected from the group consisting of fluoro and chloro, and A is an oxygen atom.

Table 1 typically exemplifies preferable compounds of formula (I).

TABLE 1

(Ia)

Exemplification Compounds

| Exemplification Compound number. | A | R⁴ |
|---|---|---|
| 1 | O | Ph |
| 2 | O | 2-FPh |
| 3 | O | 3-FPh |
| 4 | O | 4-FPh |
| 5 | O | 2,4-diFPh |
| 6 | O | 2,6-diFPh |
| 7 | O | 2,4,6-triFPh |
| 8 | O | 2-ClPh |
| 9 | O | 4-ClPh |
| 10 | O | 2,4-diClPh |
| 11 | O | 2,4,6-triClPh |
| 12 | O | 4-MePh |
| 13 | O | 4-CF₃Ph |
| 14 | O | 4-OMePh |
| 15 | O | 4-OCHF₂Ph |
| 16 | O | 2-Cl-6-FPh |
| 17 | O | 2-Cl-4-FPh |
| 18 | O | 4-Cl-2-FPh |
| 19 | S | Ph |
| 20 | S | 2-FPh |
| 21 | S | 4-FPh |
| 22 | S | 2,4-diFPh |
| 23 | S | 2,4,6-triFPh |
| 24 | S | 4-ClPh |
| 25 | S | 2,4-diClPh |
| 26 | S | 2,4,6-triClPh |
| 27 | S | 4-CF₃Ph |
| 28 | S | 2-Cl-4-FPh |
| 29 | S | 4-Cl-2-FPh |
| 30 | NH | Ph |
| 31 | NH | 4-FPh |
| 32 | NH | 2,4-diFPh |
| 33 | NH | 2,4,6-triFPh |
| 34 | NH | 4-ClPh |
| 35 | NH | 2,4-diClPh |
| 36 | NH | 4-CF₃Ph |
| 37 | NH | 2-Cl-4-FPh |
| 38 | NH | 4-Cl-2-FPh |
| 39 | O | 4-OCF₃Ph |
| 40 | O | 3-ClPh |
| 41 | O | 4-BrPh |
| 42 | O | 2,6-diClPh |
| 43 | S | 4-OCF₃Ph |
| 44 | S | 4-OCHF₂Ph |
| 45 | S | 3-FPh |
| 46 | S | 2-ClPh |
| 47 | S | 4-BrPh |
| 48 | S | 2,6-diFPh |
| 49 | S | 2,6-diClPh |
| 50 | NH | 4-OCF₃Ph |
| 51 | NH | 2-FPh |
| 52 | NH | 2-ClPh |
| 53 | NH | 2,6-diFPh |
| 54 | NH | 2,6-diClPh |
| 55 | NH | 2,4,6-triClPh |

In Table 1, the symbols Me and Ph denote the methyl and phenyl groups respectively.

The preferred compounds in Table 1 are those of exemplification compound number 1, 2, 4, 5, 7, 9, 10, 11, 13, 17, 18, 19, 21, 22, 23, 24, 25, 28, 29, 30, 31, 32, 34, 37 and 38;

the more preferred compounds are those of 1, 4, 5, 7, 9, 10, 17, 18, 21, 22, 24, 25, 31, 32 and 34;

the still more preferred compounds are those of 4, 5, 9, 10, 21, 22 and 24; and the most preferred compounds are 4: 7-(4-fluorobenzyloxy)-2,3-dimethyl-1-[(1S,2S)-2-methylcyclopropylmethyl]pyrrolo[2,3-d]pyridazine;

5: 7-(2,4-difluorobenzyloxy)-2,3-dimethyl-1-[(1S,2S)-2-methylcyclopropylmethyl]pyrrolo[2,3-d]pyridazine; and 9: 7-(4-chlorobenzyloxy)-2,3-dimethyl-1-[(1S,2S)-2-methylcyclopropylmethyl]pyrrolo[2,3-d]pyridazine.

The pyrrolopyridazine derivatives of formula (I) can be prepared by the method rated in the following reaction scheme.

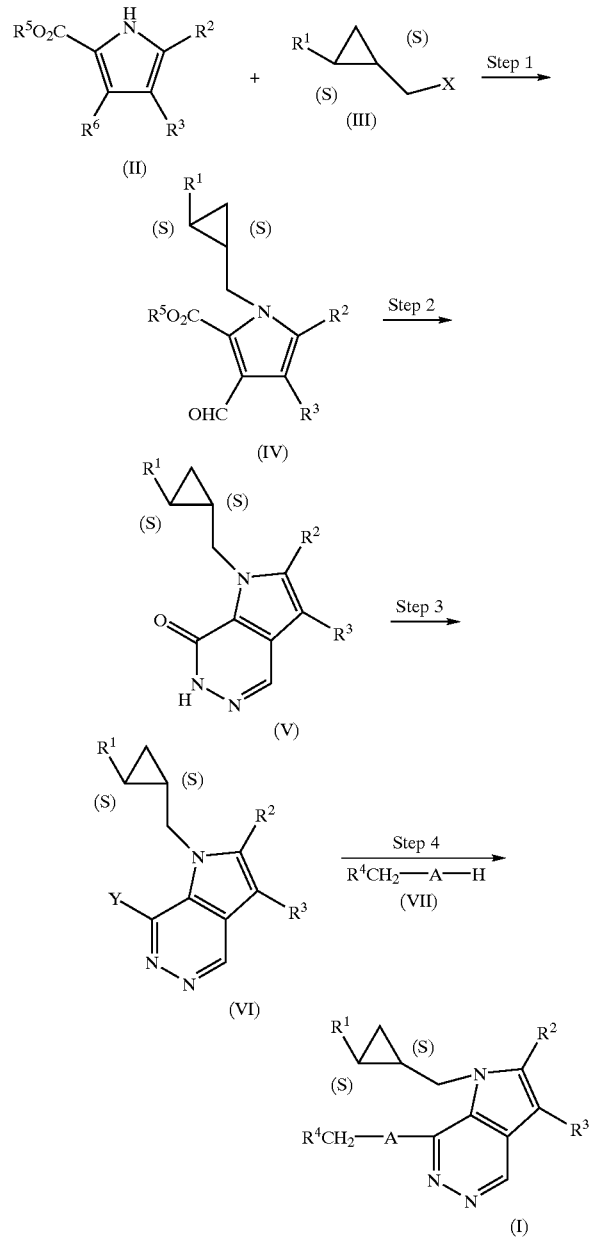

In the formulae of the compounds in the above reaction scheme, $R^1$, $R^2$, $R^3$, $R^4$ and A are as defined above, $R^5$ is a $C_1$–$C_6$ alkyl group, $R^6$ is a hydrogen atom or a formyl group, X is a halogen atom (preferably a chlorine, bromine or iodine atom) or a $C_1$–$C_6$ alkanesulfonyloxy or $C_6$–$C_{10}$ arylsulfonyloxy group such as methanesulfonyloxy, ethanesulfonyloxy, butanesulfonyloxy, benzenesulfonyloxy, toluenesulfonyloxy and naphthalenesulfonyloxy (preferably a methanesulfonyloxy, ethanesulfonyloxy, benzenesulfonyloxy or p-toluenesulfonyloxy group) and Y is a halogen atom (preferably a chlorine, bromine or iodine atom).

Step 1, in which a compound of formula (IV) is prepared, is accomplished by reaction of a compound of formula (II) with a compound of formula (III) in an inert solvent in the presence of a base. When $R^6$ is a hydrogen atom, this is followed by formylation of the reaction product.

The base used in the reaction of the compound of formula (II) with the compound of formula (III) is, for example, an alkali metal hydride such as lithium hydride, sodium hydride or potassium hydride; an alkali metal amide such as lithium amide, sodium amide or potassium amide; an alkali metal carbonate such as lithium carbonate, sodium carbonate or potassium carbonate; an alkali metal alkoxide such as lithium methoxide, sodium methoxide, sodium ethoxide or potassium tert-butoxide; an organic amine derivative such as triethylamine, tributylamine, diisopropylethylamine, N-ethylmorpholine, pyridine, picoline, 4-(N,N-dimethylamino)pyridine, quinoline, N,N-dimethylaniline, N,N-diethylaniline, 1,5-diazabicyclo[4.3.0]non-5-ene (DBN); 1,4-diazabicyclo[2.2.2]octane (DABCO) or 1,8-diazabicyclo[5.4.0]undec-7-ene (DBU); is preferably an alkali metal hydride (especially sodium hydride) or an alkali metal alkoxide (especially potassium tert-butoxide).

The inert solvent in step 1 is not limited provided that it has no adverse effect on the reaction and can dissolve the starting materials to a certain extent. Such a solvent is, for example, an aliphatic hydrocarbon such as hexane, heptane, ligroin or petroleum ether; an aromatic hydrocarbon such as benzene, toluene or xylene; a halogeno-hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a ketone such as acetone, methyl ethyl ketone, methyl isobutyl ketone, isophorone or cyclohexanone; an amide such as formamide, dimethylformamide, dimethylacetamide, N-methyl-2-pyrrolidone or hexamethylphosphoric triamide; a sulfoxide such as dimethylsulfoxide; or sulfolane; or mixtures thereof; and is preferably an ether (especially tetrahydrofuran or dioxane).

The reaction temperature of step 1 is usually in the range of from 0° C. to 250° C. (preferably from room temperature to 150° C.). The reaction time of step 1 depends on the reaction temperature and the like and is in the range of from 1 minute to 50 hours (preferably from 10 minutes to 30 hours).

A quaternary ammonium salt such as benzyltrimethylammonium chloride, tetrabutylammonium chloride or tetrabutylammonium bromide or a crown ether such as 18-crown-6 or dibenzo-18-crown-6 may be added to the reaction mixture in order to effectively carry out the reaction.

When $R^6$ is hydrogen, the subsequent formylation of the product obtained by the reaction of the compound of formula (II) with the compound of formula (III) is accomplished by reaction of the product with a Vilsmeier reagent in the presence or absence of an inert solvent.

The Vilsmeier reagent is known in the chemistry arts and is, for example, a combination of a halogenating reagent and dimethylformamide such as phosphorus oxychloride-dimethylformamide, phosphorus oxybromide-dimethylformamide or oxalyl chloride-dimethylformamide, and is preferably phosphorous oxychloride-dimethylformamide.

The inert solvent in the Vilsmeier reaction is not limited provided that it has no adverse effect on the reaction and can dissolve the starting materials to a certain extent. Such a solvent is, for example, an aromatic hydrocarbon such as benzene, toluene or xylene; a halogeno-hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane and diethylene glycol dimethyl ether; or an amide such as dimethylformamide, and is preferably a halogeno-hydrocarbon (especially methylene chloride, chloroform or dichloroethane).

The reaction temperature for the Vilsmeier reaction is usually in the range of from −20° C. to 150° C. (preferably from 0° C. to 100° C.). The reaction time depends on the reaction temperature and the like and is in the range of from 15 minutes to 12 hours (preferably from 30 minutes to 5 hours).

Step 2, in which a compound of formula (V) is prepared, is accomplished by a reaction of a compound of formula (IV) with hydrazine or a hydrate thereof in an inert solvent.

The inert solvent used in step 2 is not limited provided that it has no adverse effect on the reaction and can dissolve the starting materials to a certain extent. Such a solvent is, for example, an ether such as diethyl ether, diisopropyl ether, tetrahydrofuran, dioxane, dimethoxyethane or diethylene glycol dimethyl ether; an alcohol such as methanol, ethanol, propanol or isopropanol; an aromatic hydrocarbon such as benzene, toluene or xylene; a carboxylic acid such as acetic acid or propionic acid; an amide such as formamide, dimethylformamide, dimethylacetamide, N-methyl-2-pyrrolidone or hexamethylphosphorictriamide; an amine such as triethylamine or pyridine; water; or mixtures thereof, and is preferably an alcohol (especially ethanol) or a carboxylic acid (especially acetic acid).

The reaction temperature of step 2 is usually in the range of from −50° C. to 150° C. (preferably from −10° C. to 120° C.). The reaction time of step 2 depends on the reaction temperature and the like and is in the range of from 10 minutes to 12 hours (preferably from 30 minutes to 5 hours).

Step 3, in which a compound of formula (VI) is prepared, is accomplished by reaction of a compound of formula (V) with a halogenating reagent in the presence or absence of an inert solvent.

The halogenating reagent in this step is, for example, phosphorus oxychloride, phosphorus oxybromide, thionyl chloride, thionyl bromide, oxalyl chloride, phosphorus pentachloride or phosphorus pentabromide, preferably phosphorus oxychloride or thionyl chloride. A large excess of the halogenating reagent can be used as a solvent in this step.

The inert solvent in step 3 is not limited provided that it has no adverse effect on the reaction and can dissolve the starting materials to a certain extent. Such a solvent is, for example, an aromatic hydrocarbon such as benzene, toluene or xylene; a halogeno-hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an amide such as dimethylformamide, dimethylacetamide or N-methyl-2-pyrrolidone; or a sulfoxide such as dimethylsulfoxide; and is preferably a halogeno-hydrocarbon (especially methylene chloride or dichloroethane).

The reaction temperature of step 3 is usually in the range of from 0° C. to 150° C. (preferably from room temperature to 120° C.). The reaction time of step 3 depends on the reaction temperature and the like and is in the range of from 30 minutes to 12 hours (preferably from 1 hour to 6 hours).

An organic amine derivative such as triethylamine, tributylamine, diisopropylethylamine, N-ethylmorpholine, pyridine, picoline or 4-(N,N-dimethylamino)pyridine may be added to the reaction mixture in order to effectively carry out the reaction.

Step 4, in which a desired compound of formula (I) of the present invention is prepared, is accomplished by reaction of a compound of formula (VI) with a compound of formula (VII) in the presence of a base in an inert solvent in a similar procedure to that described in step 1.

Each desired product of steps 1, 2, 3, and 4 may be isolated by conventional procedures from the reaction mixture. For example, it may be obtained 1) by filtration of the reaction mixture when insoluble material exists in the reaction mixture, followed by evaporation of the solvent of the filtrate; or by 1) concentration of the reaction mixture, 2) partition of the residue between water and an appropriate organic solvent immiscible with water, 3) drying the extract over anhydrous magnesium sulfate and the like, followed by 4) concentration of the extract. The desired compound is, if necessary, further purified by conventional procedures such as recrystallization, column chromatography and the like.

The desired optically active compound (1S and 2S configuration) can also be prepared by optical resolution of the racemic product (the racemic form of the compound of any one of formulae (I), (IV), (V) or (VI)), which is obtained by the same procedure using the racemic compound of formula (IIIa) (a mixture of 1S, 2S and 1R, 2R configuration) in step 1 instead of the optically active compound of formula (IIIa).

(IIIa)

A method of optical resolution can be appropriately selected from conventional procedures, for example, column chromatography for optical resolution, preferential crystallization, or resolution of diastereomeric salts.

The compound of formula (I) can be converted into its pharmaceutically acceptable salt by treatment with an acid. For example, it can be obtained by reaction of the compound of formula (I) with an acid in an inert solvent (a preferred solvent is an ether such as diethyl ether, tetrahydrofuran or dioxane; an alcohol such as methanol, ethanol or propanol; or a halogeno-hydrocarbon such as methylene chloride or chloroform) for from 5 minutes to 1 hour, followed by concentration.

The starting compounds of formulae (II), (III) and (IIIa) are known or prepared by methods known to the skilled person (for example, Japanese Patent Application Publication Hei 7–247285, Monatschefte fur Chemie 104, 925 (1973), J. Chem. Soc. Perkin. Trans. II 287 (1979) and the like).

The compounds of formula (I) of this invention exhibit potent gastric acid secretion inhibition activity, protective activity of gastric mucous membranes and potent antibacterial activity against *Helicobacter pylori* and excellent properties as a medicament. The compounds of formula (I) are useful as a medicament, especially a useful prophylactic or therapeutic (preferably therapeutic) agent for ulcerative diseases such as peptic ulcer, acute or chronic gastric ulcer, gastritis, reflux esophagitis, gastroesophageal reflux disorder, dyspepsia, gastric hyperacidity or Zollinger-Ellison syndrome, and as a prophylactic or therapeutic (preferably therapeutic) agent for bacterial infections arising from *Helicobacter pylori*.

When used as a medicament, especially as a prophylactic or therapeutic agent for the diseases described above, a compound of formula (I) or a pharmaceutically acceptable salt thereof (the active ingredient) can be administered alone or can be presented as part of a pharmaceutical formulation. The pharmaceutical formulation is prepared by blending the active ingredient with appropriate pharmaceutically acceptable carriers such as excipients, diluents and the like, followed by formulation in the form of tablets, capsules, granules, powders or syrups and the like for oral administration or in the form of injections and the like for parenteral administration (preferably oral administration).

The production of such pharmaceutical formulations is carried out according to general techniques known to those skilled in the art, using additives such as an excipient, a binder, a disintegrant, a lubricant, a stabilizer, a corrigent, a diluent and a solvent for injections.

The excipient is, for example, a sugar derivative such as lactose, sucrose, glucose, mannitol or sorbitol; a starch derivative such as corn starch, potato starch, α-starch, dextrin or carboxymethyl starch; a cellulose derivative such as crystalline cellulose, low-substituted hydroxypropyl cellulose, hydroxypropylmethyl cellulose, carboxymethyl cellulose, calcium carboxymethyl cellulose or internally bridged sodium carboxymethyl cellulose; gum arabic; dextran; pullulan; a silicate derivative such as light silicic acid anhydride, synthetic aluminium silicate or magnesium aluminate meta-silicate; a phosphate derivative such as calcium phosphate; a carbonate derivative such as calcium carbonate; or a sulfate derivative such as calcium sulfate; and the like.

The binder is, for example, one of the excipients described above; gelatin; polyvinylpyrrolidone; macrogol (trademark) and the like.

The disintegrant is, for example, one of the excipients described above, a chemically modified starch or cellulose derivative such as sodium croscarmellose, sodium carboxymethyl starch; or bridged polyvinylpyrrolidone; and the like.

The lubricant is, for example, talc; stearic acid; a metal salt of stearic acid such as calcium stearate or magnesium stearate; colloidal silica; a wax such as bee gum and spermaceti; boric acid; glycol; a carboxylic acid such as fumaric acid or adipic acid; a sodium carboxylate such as sodium benzoate; a sulfate such as sodium sulfate; leucine; a laurylsulfate such as sodium laurylsulfate and magnesium laurylsulfate; a silicic acid derivative such as silicic acid anhydride or silicic acid hydrate; one of the starch derivatives described above in relation to the excipients; and the like.

The stabilizer is, for example, a p-hydroxybenzoate derivative such as methylparaben and propylparaben; an alcohol such as chlorobutanol, benzyl alcohol or phenylethyl alcohol; benzalkonium chloride; a phenol derivative such as phenol or cresol; thimerosal; dehydroacetic acid; sorbic acid; and the like.

The corrigent is, for example, a sweetening, souring or flavoring agent, which are conventionally used; and the like.

The solvent for injection is, for example, water, ethanol, glycerin and the like.

Suitable dosage levels will depend on the condition of disease, the age of the patient and the like, but typically suitable dosage levels for an active ingredient of the present invention are from 1 mg (preferably 5 mg) to 1000 mg (preferably 500 mg) for oral administration and from 0.1 mg (preferably 1 mg) to 500 mg (preferably 300 mg) for intravenous administration per unit dose, per day, for an adult human, respectively. The dosages described above are preferably administered from one time to six times throughout the day, depending on the condition of disease.

EXAMPLES

The following Examples, Test Examples and Formulation Examples are intended to further illustrate the present invention and are not intended to limit the scope of the invention.

Example 1

7-(4-Fluorobenzyloxy)-2,3-dimethyl-1-[(1S,2S)-2-methylcyclopropylmethyl]pyrrolo[2,3-d]pyridazine (a) Methyl 3-formyl-4,5-dimethyl-1-[(1S,2S)-2-methylcyclopropylmethyl]pyrrole-2-carboxylate Potassium tert-butoxide (3.94 g, 35.1 mmol) was added to a solution of methyl 3-formyl-4,5-dimethylpyrrole-2-carboxylate (5.79 g, 31.9 mmol) and 18-crown-6 (0.41 g, 1.55 mmol) in tetrahydrofuran (130 ml) and the mixture was stirred at room temperature for 1 hour. After dropwise addition over 30 minutes of (1S,2S)-2-methylcyclopropylmethyl bromide (5.71 g, 38.3 mmol) to the reaction mixture at 50° C., the mixture was heated under reflux for 3 hours. Potassium tert-butoxide (0.36 g, 3.22 mmol) and (1S,2S)-2-methylcyclopropylmethyl bromide (0.48 g, 3.21 mmol) was further added to the mixture and this mixture was heated for 1 hour. The reaction mixture was poured into iced water and extracted with ethyl acetate. The extract was washed with water and saturated aqueous sodium chloride solution and then dried over anhydrous magnesium sulfate. The solvent was removed in vacuo to afford the desired compound (8.26 g, 100%) as a pale brown oil.

Mass spectrum (Cl, m/z): 250 (M$^+$+1)

NMR spectrum (CDCl$_3$, δ ppm):0.25 (dt;J=8 Hz,5 Hz,1H), 0.48 (dt; J=8 Hz,5 Hz,1H), 0.71–0.80(m,1H), 0.82–0.89(m,1H), 1.00(d;J=6 Hz,3H), 2.20(s,3H), 2.26(s, 3H), 3.89(s,3H,4.25(d;J=7 Hz,2H), 10.43(s,1H).

Optical rotation: $[\alpha]_D^{20}$=+17.6° (c=1.02,EtOH).

(b) 2,3-Dimethyl-1-[(1S,2S)-2-methylcyclopropylmethyl]-6,7-dihydropyrrolo[2,3-d]pyridazin-7-one Hydrazine hydrate (1.92 g, 38.4 mmol) was added to a solution of methyl 3-formyl-4,5-dimethyl-1-[(1S,2S)-2-methylcyclopropylmethyl]pyrrole-2-carboxylate (7.96 g, 31.9 mmol) in acetic acid (38 ml) and the mixture was stirred at 90° C. for 1 hour. After this time, the reaction mixture was cooled to room temperature, poured into iced water and filtered. The crude crystals were washed with water and dissolved in a mixture of chloroform and methanol (9:1). The organic layer was separated, washed with saturated aqueous sodium chloride solution and then dried over anhydrous magnesium sulfate. The solvent was removed in vacuo and to the residue was added a mixture of toluene and hexane. The precipitate was collected by filtration to afford the desired compound (7.02 g, 95.0%) as a pale yellowish white powder.

Mass spectrum (Cl, m/z): 232 (M$^+$+1)

NMR spectrum (CDCl$_3$, δ ppm):0.22 (dt; J=8 Hz, 5 Hz, 1H), 0.64 (dt, J=8 Hz, 5 Hz, 1H), 0.86–0.95 (m, 2H), 0.98 (d; J=5 Hz, 3H), 2.21 (s,3H), 2.35 (s,3H), 4.44 (d; J=7 Hz, 2H), 8.05 (s,1H), 9.97 (s,1H).

Optical rotation: $[\alpha]_D^{20}$=+11.2° (c=0.50, EtOH).

(c) 7-Chloro-2,3-dimethyl-1-[(1S,2S)-2-methylcyclopropylmethyl]pyrrolo[2,3-d]pyridazine Phosphorus oxychloride (55 ml, 590 mmol) was added to 2,3-dimethyl-1-[(1S,2S)-2-methylcyclopropylmethyl]-6,7-dihydropyrrolo[2,3-d]pyridazin-7-one (6.95 g, 30.1 mmol) and the mixture was stirred at 90° C. for 3.5 hours. After this time the reaction mixture was cooled to room temperature and poured dropwise into iced water. The aqueous solution was neutralized with 5N aqueous sodium hydroxide solution and extracted with methylene chloride. The extract was washed with water, dried over anhydrous magnesium sulfate and then concentrated in vacuo. Hexane was added to the residue and the precipitate was collected by filtration to afford the desired compound (6.90 g, 92.0%) as a pale yellow powder.

Mass spectrum (Cl, m/z): 250 (M$^+$+1)

NMR spectrum (CDCl$_3$, δ ppm): 0.29 (dt; J=8 Hz, 5 Hz, 1H), 0.54 (dt; J=8 Hz, 5 Hz, 1H), 0.73–1.02 (m, 5H), 2.30 (s, 3H), 2.43 (s, 3H), 4.44 (d; J=6 Hz, 2H), 9.15 (s, 1H).

Optical rotation: $[\alpha]_D^{20}$=+12.3° (c=1.01, EtOH).

(d) 7-(4-Fluorobenzyloxy)-2,3-dimethyl-1-[(1S,2S)-2-methylcyclopropylmethyl]pyrrolo[2,3-d]pyridazine A solution of p-fluorobenzyl alcohol (1.45 g, 11.5 mmol) in tetrahydrofuran (2 ml) was added dropwise to a solution of sodium hydride (0.26 g, 10.8 mmol) in tetrahydrofuran (6 ml) and the mixture was stirred at room temperature for 30 minutes. A solution of 7-chloro-2,3-dimethyl-1-[(1S,2S)-2-methylcyclopropylmethyl]pyrrolo[2,3-d]pyridazine (2.50 g, 10.0 mmol) in tetrahydrofuran (13 ml) was added dropwise to the reaction mixture and the mixture was heated under reflux for 3 hours. After this time the reaction mixture was poured into iced water and extracted with ethyl acetate. The extract was washed with saturated aqueous sodium chloride solution, dried over anhydrous magnesium sulfate and then concentrated in vacuo. Hexane was added to the residue, and the precipitate was collected by filtration and then recrystallized from a mixture of ethyl acetate and hexane to afford the title compound (2.25 g, 66.4%) as pale brown crystals.

Mp: 114–115° C.

Mass spectrum (Cl, m/z): 340 (M$^+$+1)

NMR spectrum (CDCl$_3$, δ ppm): 0.14 (dt; J=8 Hz, 5 Hz, 1H), 0.39 (dt; J=8 Hz, 5 Hz, 1H), 0.59–0.65 (m, 1H), 0.76–0.85 (m,1H), 0.89 (d; J=6 Hz, 3H), 2.26 (s, 3H), 2.36 (s, 3H), 4.13 (dd;J=15 Hz, 7 Hz, 1H), 4.27 (dd; J=15 Hz, 6 Hz, 1H), 5.63 (d; J=12 Hz, 1H), 5.68 (d; J=12 Hz, 1H), 7.05–7.12 (m, 2H), 7.47–7.52 (m, 2H), 8.96 (s, 1H).

Optical rotation: $[\alpha]_D^{20}$=+17.9° (c=0.50, EtOH).

Example 2

Methyl 3-formyl-4,5-dimethyl-1-[(1S,2S)-2-methylcyclopropylmethyl]pyrrole-2-carboxylate (a) Methyl 4,5-dimethyl-1-[(E)-2-methylcyclopropylmethyl]pyrrole-2-carboxylate Potassium tert-butoxide (18.33 g, 164 mmol) was added to a solution of methyl 4,5-dimethylpyrrole-2-carboxylate (25.02 g, 163 mmol) and 18-crown-6 (3.19 g, 12.1 mmol) in tetrahydrofuran (150 ml) and the mixture was stirred at room temperature for 1 hour. To this mixture was added a solution of (E)-2-methylcyclopropylmethyl bromide (racemate, 12.70 g, 85.2 mmol) and the mixture was heated under reflux for 7 hours. After this time the reaction mixture was poured into iced water and extracted with ethyl acetate. The extract was washed with water and saturated aqueous sodium chloride solution, dried over anhydrous magnesium sulfate and then concentrated in vacuo. The residue was chromatographed on a column using toluene as the eluant to afford the desired compound (racemate, 13.50 g, 71.6%) as a brown oil.

Mass spectrum (Cl, m/z):222(M$^+$+1)

NMR spectrum (CDCl$_3$,δ ppm):0.20 (dt;J=8 Hz, 5 Hz, 1H), 0.48 (dt; J=8 Hz, 5 Hz, 1H), 0.67–0.93 (m, 2H), 0.98 (d;J=6 Hz, 3H), 2.01 (s, 3H), 2.18 (s, 3H),3.76 (s, 3H), 4.21 (d;J=7 Hz, 2H), 6.76 (s, 1H).

(b) Methyl 4,5-dimethyl-1-[(1S,2S)-2-methylcyclopropylmethyl]pyrrole-2-carboxylate Methyl (E)-4,5-dimethyl-1-(2-methylcyclopropylmethyl) pyrrole-2-carboxylate (10 g) was purified by high pressure liquid chromatography on a column (CHIRALCEL OJ (50φ×500 mm, a product of Daicel Chemical Industries, Ltd.) using hexane/2-propanol=1000/1 as the eluant at 25 ml per minute to afford the title [(S,S) form] compound (3.33 g) and the [(R,R) form] compound (3.97 g), which is the antipode of the [(S,S) form] compound.

[(S,S) form] compound:
Mass spectrum (Cl, m/z): 222 (M$^+$+1)
NMR spectrum (CDCl$_3$, δ ppm): 0.20 (dt; J=8 Hz, 5 Hz, 1H), 0.48 (dt; J=8 Hz, 5 Hz, 1H), 0.66–0.80 (m, 1H), 0.82–0.91 (m, 1H), 0.98 (d; J=6 Hz, 3H), 2.01 (s,3H), 2.18 (s,3H), 3.76 (s,3H), 4.21 (d;J=7 Hz, 2H), 6.76 (s,1H).
Optical rotation: $[\alpha]_D^{20}$=+17.6° (c=1.00, EtOH).

[(R,R) form] compound:
Mass spectrum (Cl, m/z): 222 (M$^+$+1)
NMR spectrum (CDCl$_3$, δ ppm): 0.20 (dt; J=8 Hz, 5 Hz, 1H), 0.48 (dt; J=8 Hz, 5 Hz, 1H),
0.66–0.80 (m, 1H), 0.82–0.91 (m, 1H), 0.98 (d;J=6 Hz, 3H), 2.01 (s, 3H), 2.18 (s, 3H),
3.77 (s, 3H), 4.21(d; J=7 Hz, 2H), 6.76 (s, 1H).
Optical rotation: $[\alpha]_D^{20}$=−17.0° (C=1.01, EtOH).

(c) Methyl 3-formyl-4,5-dimethyl-1-[(1S,2S)-2-methylcyclopropylmethyl]pyrrole-2-carboxylate Phosphorous oxychloride (2.15 g, 14 mmol) was added to a solution of dimethylformamide (1.10 g, 15 mmol) in toluene (2 ml) and the mixture was stirred at room temperature for 30 minutes. To this mixture was added a solution of methyl 4,5-dimethyl-1-[(1S,2S)-2-methylcyclopropylmethyl]pyrrole-2-carboxylate (2.21 g, 10 mmol) in toluene (6 ml) and the mixture was then heated at 80° C. for 10 hours. After this time, the reaction mixture was poured into water and neutralized with saturated aqueous sodium hydrogencarbonate solution. The organic layer was separated and was washed with saturated aqueous sodium chloride solution, dried over anhydrous magnesium sulfate and then concentrated in vacuo. The residue was chromatographed on a column using ethyl acetate/hexane=10/1 as the eluant to afford the title compound (1.95 g, 78.2%) as a pale yellow oil.

Example 3
7-(4-Fluorobenzyloxy)-2,3-dimethyl-1-[(1S,2S)-2-methylcyclopropylmethyl]pyrrolo[2,3-d]pyridazine (a) 7-(4-Fluorobenzyloxy)-1-[(E)-2-methylcyclopropylmethyl]-2,3-dimethylpyrrolo[2,3-d]pyridazine (racemate)

A reaction was carried out in a similar manner to that described in Example 1 using (E)-2-methylcyclopropylmethyl bromide (racemate) instead of (1S,2S)-2-methylcyclopropylmethyl bromide to afford the desired compound (56%).

Mp: 120–122° C.
Mass spectrum (Cl, m/z): 340 (M$^+$+1)
NMR spectrum (CDCl$_3$, δ ppm): 0.14 (dt; J=8 Hz, 5 Hz, 1H), 0.39 (dt; J=8 Hz, 5 Hz, 1H), 0.59–0.65 (m, 1H), 0.76–0.85 (m, 1H), 0.89 (d; J=6 Hz, 3H), 2.26 (s, 3H), 2.36 (s, 3H), 4.13 (dd; J=15 Hz, 7 Hz, 1H), 4.27 (dd; J=15 Hz, 6 Hz, 1H), 5.63 (d; J=12 Hz, 1H), 5.68 (d; J=12 Hz, 1H), 7.05–7.12 (m, 2H), 7.47–7.52 (m, 2H), 8.96 (s,1H).

(b) 7-(4-Fluorobenzyloxy)-2,3-dimethyl-1-[(1S,2S)-2-methylcyclopropylmethyl]pyrrolo[2,3-d]pyridazine 7-(4-Fluorobenzyloxy)-1-[(E)-2-methylcyclopropylmethyl]-2,3-dimethylpyrrolo[2,3-d] pyridazine (racemate, 25 g) was purified by high pressure liquid chromatography on a column (CHIRALCEL OJ (50φ×500 mm, a product of Daicel Chemical Industries, Ltd.) using hexane/ethanol=90/10 as the eluant at 25 ml per minute and recrystallized from ethyl acetate to afford the title [(S,S) form] compound (8.54 g) and the [(R,R) form] compound (7.60 g), which is the antipode of the [(S,S) form] compound.

[(S,S) form] compound:
Mp: 114–115° C.
Mass spectrum (Cl, m/z): 340 (M$^+$+1)
NMR spectrum (CDCl$_3$, δ ppm): 0.14 (dt; J=8 Hz, 5 Hz, 1H), 0.39 (dt; J=8 Hz, 5 Hz, 1H), 0.59–0.65 (m, 1H), 0.76–0.85 (m, 1H), 0.89 (d; J=6 Hz, 3H), 2.26 (s, 3H), 2.36 (s, 3H), 4.13 (dd; J=15 Hz, 7 Hz, 1H), 4.27 (dd; J=15 Hz, 6 Hz, 1H), 5.63 (d; J=12 Hz, 1H), 5.68 (d; J=12.2 Hz, 1H), 7.05–7.12 (m,2H), 7.47–7.52 (m,2H), 8.96 (s, 1H).
Optical rotation: $[\alpha]_D^{20}$=+19.0° (c=0.99, MeOH).

[(R,R) form] compound:
Mp: 114–115° C.
Mass spectrum (Cl, m/z): 340 (M$^+$+1)
NMR spectrum (CDCl$_3$, δ ppm): 0.15 (dt; J=8 Hz, 5 Hz, 1H), 0.39 (dt; J=8 Hz, 5 Hz, 1H), 0.58–0.66 (m, 1H), 0.78–0.85 (m, 1H), 0.89 (d; J=6 Hz, 3H), 2.26 (s, 3H), 2.37 (s, 3H), 4.13 (dd; J=15 Hz, 7 Hz, 1H), 4.27 (dd; J=15 Hz, 6 Hz, 1H), 5.63 (d; J=12 Hz, 1H), 5.68 (d; J=12 Hz, 1H), 7.06–7.11 (m, 2H), 7.49–7.52 (m, 2H), 8.97 (s, 1H).
Optical rotation: $[\alpha]_D^{20}$=−18.8° (c=0.98, MeOH).

Test Example 1
Test on Activity of Proton Potassium-adenosine Triphosphatase (H$^+$·K$^+$-ATPase)

A microsomal fraction prepared in accordance with the method of Sachs, et al. [J. Bio., Chem., 251, 7690 (1976)] by homogenizing a fresh gastric mucosal layer of swine and then subjecting the homogenate to density gradient ultra centrifugation was employed as a proton potassium-adenosine triphosphatase preparation. A solution (10 μl) of a test compound dissolved in dimethyl sulfoxide was added to 0.75 ml of a 70 mM tris-hydrochloric acid buffer (5 mM magnesium chloride, 20 mM potassium chloride, pH=6.85) containing 30 to 80 μg/ml, in terms of a protein concentration, of an enzyme preparation. The mixture was incubated with 200 times/min of agitation at 37° C. for 45 minutes. The enzymatic reaction was started by adding 0.25 ml of a 8 mM solution of disodium adenosine triphosphate. After this enzymatic reaction was continued for 20 minutes, 1 ml of a 10% trichloroacetic acid-activated charcoal (100 mg) solution was added to terminate the reaction. The reaction mixture was centrifuged (at 4° C. and 3000 rpm) for 15 minutes. Inorganic phosphoric acid formed by the hydrolysis of adenosine triphosphate in the supernatant was subjected to colorimetry by the method of Yoda, et al. [Biochem. Biophys, Res. Commun., 40, 880 (1970)]. The amount of inorganic phosphoric acid in a reaction mixture free from potassium chloride was also measured. By subtracting this amount from the amount of inorganic phosphoric acid in the presence of potassium chloride, proton potassium-adenosine triphosphatase activity was determined. An inhibition ratio (%) was determined from the active value of the control and the active value of the test compound at each concentration, whereby a 50% inhibitory concentration (IC$_{50}$ μg/ml) against proton-potassium-adenosine triphosphatase was determined. As a result, the compound of Example 1 had a 50% inhibitory concentration (IC$_{50}$) not greater than 0.1 μg/ml, exhibiting excellent activity.

Test Example 2
Antibacterial Action Against *Helicobacter pylori*

The antibacterial activity of the invention compound was evaluated by using *Helicobacter pylori* strains 9470, 9472 and 9474 and determining MIC (Minimum Inhibitory Concentration) of the invention compound against *Helicobacter pylori*.

*Helicobacter pylori* was cultured by plating for 4 days. A medium was prepared by dissolving Brain Heart Infusion Agar (product of Difco Laboratories) in a prescribed amount of distilled water, sterilizing in an autoclave, adding equine blood (product of Nippon Seibutsu Zairyo) to give its concentration of 7% and then solidifying the mixture.

Under microaerophilic conditions, *Helicobacter pylori* which had been cultured at 37° C. for 4 days was suspended in physiological saline to give its viable count of about $10^8$ CFU/ml. The suspension was then diluted to 100 times and a portion (about 10 μl) of the diluted suspension was inoculated in a medium for measuring MIC. The medium employed for measuring MIC has the same composition as the preculture medium. A compound of this invention was dissolved in dimethyl sulfoxide (DMSO) and two-fold serial dilutions were made with sterilized water. After mixing the solution and the medium in a ratio of 1:99, a solidified product in the Petri dish was employed as an MIC measuring medium. In a similar manner to that employed for the preculture, *Helicobacter pylori* was cultured at 37° C. for 3 days under microaerophilic conditions. After completion of the culturing, growth of the bacteria at the inoculated portion was visually observed. The minimum concentration of a compound of this invention at which no bacteria growth was observed was designated as MIC (μg/ml). The compound of Example 1 exhibited excellent antibacterial activity, that is, MIC not greater than 12.5 μg/ml.

Test Example 3
Gastric Acid Secretion Inhibition Activity

After groups of rats, each group consisting of 3 to 5 rats, were fasted overnight, they were subjected to midline abdominal incision and their pylorus was ligated under anesthesia with ether. The stomach and duodenum were returned to their original positions in the body, followed by closing at the abdominal incision part. A predetermined amount of a test compound was suspended in an aqueous solution containing 0.5% of sodium carboxymethylcellulose and 0.4% of Tween 80 (Polysorbate 80). The resulting suspension was orally administered to the rats. As a control, an aqueous suspension (suspending solvent) containing 0.5% of sodium carboxymethylcellulose and 0.4% of Tween 80 (Polysorbate 80) was orally administered to other rats. Four hours after administration of the test compound or suspending solvent, the rats were sacrificed by inhalation of $CO_2$ gas. They were subjected to abdominal incision to remove their stomach. The content of the stomach was collected in a glass-made graduated centrifuge tube. After centrifugation, the amount (ml) of the supernatant and the amount (ml) of the precipitate were measured. The precipitate of the amount exceeding 0.5 ml was regarded as coprophage and removed from the data. The supernatant (100 μl) was poured into a test tube. Distilled water (4 ml) was added to the solution, and the solution was titrated to pH 7.0 with 0.01 N sodium hydroxide. A standard acid concentration solution obtained by adding 4 ml of distilled water to 100 μl of 0.1 N hydrochloric acid was titrated in a similar manner. The acid concentration of gastric juice (mEq/l), gastric acid output (AO, μEq/hr) and inhibition ratio (%) were calculated in accordance with the following equations:

Acid concentration of gastric juice (*m*Eq/l)=*A*/*B*×100

A: amount (ml) of sodium hydroxide required for titration of 100 μl of supernatant B: amount (ml) of sodium hydroxide required for titration of 100 μl of 0.1 N hydrochloric acid Gastric acid output (AO, μEq/hr)=amount (ml) of supernatant of gastric juice×acid concentration of gastric juice (*m*Eq/l)/4

Inhibition ratio (%)=(*C*−*D*)/*C*×100

C: AO (μEq/hr) of suspending-solvent-administered group

D: AO (μEq/hr) of test-compound-administered group

A 50% inhibitory dose ($ID_{50}$ mg/kg) was determined from a dose-inhibition ratio curve on which an inhibition ratio at each dose (0.3 mg/kg, 1 mg/kg, 3 mg/kg and 10 mg/kg) versus logarithmic dose was drawn in accordance with the least squares. The results are shown in Table 2.

TABLE 2

Inhibitory effects on gastric acid secretion

| Test compound | 50% inhibitory dose ($ID_{50}$, mg/kg) against gastric acid secretion |
|---|---|
| Compound of Example 1 | 0.52 |
| Compound A | 1.64 |

Compound A: A 1:1 mixture of Compound of Example 1 and its antipode (racemate: Compound of Example 57 of Japanese Patent Application Laid-Open No. 7–247285)

From the results shown in Table 2, it has been found that the compound of Example 1 exhibited effects about 3 times stronger than its racemate.

Formulation Example 1
Tablets

| The compound of Example 1 | 30.0 mg |
|---|---|
| Lactose | 144.0 mg |
| Corn starch | 25.0 mg |
| Magnesium stearate | 1.0 mg |
| | 200.0 mg |

A tablet is prepared using the ingredients above. The components are blended and compressed by a tablet machine to form a tablet weighing 200 mg. The tablet may be coated if necessary, for example, to form a sugar-coated tablet.

What is claimed is:

1. An optically active pyrrolopyridazine compound of formula (I) or a pharmaceutically acceptable salt thereof:

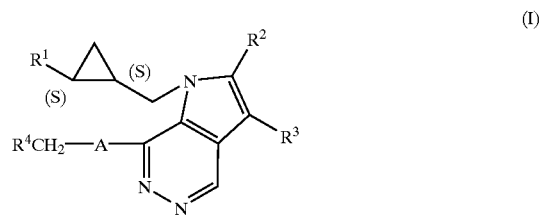

wherein:
$R^1$ is a $C_1$–$C_6$ alkyl group;
$R^2$ and $R^3$ are each independently a $C_1$–$C_6$ alkyl group;

R⁴ is a $C_6$–$C_{10}$ aryl group which is unsubstituted or substituted with one or more substituents selected from the group consisting of $C_1$–$C_6$ alkyl, halogeno $C_1$–$C_6$ alkyl, $C_1$–$C_6$ alkoxy, halogeno $C_1$–$C_6$ alkoxy and halogen; and A is an imino group, an oxygen atom or a sulfur atom.

2. The optically active pyrrolopyridazine compound or a pharmaceutically acceptable salt thereof according to claim 1, wherein R¹ is a $C_1$–$C_4$ alkyl group.

3. The optically active pyrrolopyridazine compound or a pharmaceutically acceptable salt thereof according to claim 1, wherein R¹ is a methyl group.

4. The optically active pyrrolopyridazine compound or a pharmaceutically acceptable salt thereof according to claim 1, wherein R² and R³ are each independently a $C_1$–$C_4$ alkyl group.

5. The optically active pyrrolopyridazine compound or a pharmaceutically acceptable salt thereof according to claim 1, wherein R² and R³ are each methyl groups.

6. The optically active pyrrolopyridazine compound or a pharmaceutically acceptable salt thereof according to claim 1, wherein R⁴ is a phenyl group which is substituted with 1 to 3 substituents selected from the group consisting of $C_1$–$C_4$ alkyl, halogeno $C_1$–$C_4$ alkyl, $C_1$–$C_4$ alkoxy, halogeno $C_1$–$C_4$ alkoxy, fluoro, chloro and bromo.

7. The optically active pyrrolopyridazine compound or a pharmaceutically acceptable salt thereof according to claim 1, wherein R⁴ is a phenyl group which is substituted with 1 to 3 substituents selected from the group consisting of methyl, trifluoromethyl, methoxy, trifluoromethoxy, difluoromethoxy, fluoro, chloro and bromo.

8. The optically active pyrrolopyridazine compound or a pharmaceutically acceptable salt thereof according to claim 1, wherein R⁴ is a phenyl group which is substituted with 1 or 2 substituents selected from the group consisting of fluoro and chloro at one or more positions of the phenyl ring selected from the group consisting of the 2-position, 4-position and 6-position.

9. The optically active pyrrolopyridazine compound or a pharmaceutically acceptable salt thereof according to claim 1, wherein R⁴ is a phenyl group which is substituted with 1 or 2 substituents selected from the group consisting of fluoro and chloro at the 4-position or at the 2- and 4-positions of the phenyl group.

10. The optically active pyrrolopyridazine compound or a pharmaceutically acceptable salt thereof according to claim 1, wherein A is an oxygen atom or a sulfur atom.

11. The optically active pyrrolopyridazine compound or a pharmaceutically acceptable salt thereof according to claim 1, wherein A is an oxygen atom.

12. The optically active pyrrolopyridazine compound or a pharmaceutically acceptable salt thereof according to claim 1, wherein:

R¹ is a $C_1$–$C_4$ alkyl group;

R² and R³ are each independently $C_1$–$C_4$ alkyl groups;

R⁴ is a phenyl group substituted with 1 to 3 substituents selected from the group consisting of $C_1$–$C_4$ alkyl, halogeno $C_1$–$C_4$ alkyl, $C_1$–$C_4$ alkoxy, halogeno $C_1$–$C_4$ alkoxy, fluoro, chloro and bromo; and A is an oxygen atom or a sulfur atom.

13. The optically active pyrrolopyridazine compound or a pharmaceutically acceptable salt thereof according to claim 1, wherein:

R¹ is a methyl group;

R² and R³ are each methyl groups;

R⁴ is a phenyl group substituted with 1 to 3 substituents selected from the group consisting of methyl, trifluoromethyl, methoxy, trifluoromethoxy, difluoromethoxy, fluoro, chloro and bromo; and A is an oxygen atom or a sulfur atom.

14. The optically active pyrrolopyridazine compound or a pharmaceutically acceptable salt thereof according to claim 1, wherein:

R¹ is a methyl group;

R² and R³ are each methyl groups;

R⁴ is a phenyl group substituted at one or more positions selected from the group consisting of the 2-position, 4-position and 6-position with 1 or 2 substituents selected from the group consisting of fluoro and chloro; and A is an oxygen atom.

15. The optically active pyrrolopyridazine compound or a pharmaceutically acceptable salt thereof according to claim 1, wherein:

R¹ is a methyl group;

R² and R³ are each methyl groups;

R⁴ is a phenyl group substituted at the 4-position with a substituent selected from the group consisting of fluoro and chloro or a phenyl group substituted at the 2- and 4-positions with two substituents selected from the group consisting of fluoro and chloro; and A is an oxygen atom.

16. The optically active pyrrolopyridazine compound or a pharmaceutically acceptable salt thereof according to claim 1, wherein the compound is 7-(4-fluorobenzyloxy)-2,3-dimethyl-1-[(1S,2S)-2-methylcyclopropylmethyl]pyrrolo[2,3-d]pyridazine.

17. The optically active pyrrolopyridazine compound or a pharmaceutically acceptable salt thereof according to claim 1, wherein the compound is 7-(2,4-difluorobenzyloxy)-2,3-dimethyl-1-[(1S,2S)-2-methylcyclopropylmethyl]pyrrolo[2,3-d]pyridazine.

18. The optically active pyrrolopyridazine compound or a pharmaceutically acceptable salt thereof according to claim 1, wherein the compound is 7-(4-chlorobenzyloxy)-2,3-dimethyl-1-[(1S,2S)-2-methylcyclopropylmethyl]pyrrolo[2,3-d]pyridazine.

19. A pharmaceutical composition for the treatment or prevention of an ulcerative disease or for the treatment or prevention of *Helicobacter pylori* infection comprising a pharmaceutically effective amount of an active ingredient together with a pharmaceutically acceptable carrier therefor, wherein said active ingredient is an optically active pyrrolopyridazine compound or a pharmaceutically acceptable salt thereof as claimed in any one of claims 1 to 18.

20. A method for the treatment or prevention of an ulcerative disease in a warm-blooded animal comprising administering to said warm-blooded animal in need of said treatment or prevention a pharmaceutically effective anti-ulcerative amount of an optically active pyrrolopyridazine compound or a pharmaceutically acceptable salt thereof as claimed in any one of claims 1 to 18.

21. The method according to claim 20, wherein said warm-blooded animal is a human.

22. A method for the treatment or prevention of an ulcerative disease in a warm-blooded animal, the ulcerative disease being selected from the group consisting of peptic ulcer, acute gastric ulcer, chronic gastric ulcer, gastritis, reflux esophagitis, gastroesophageal reflux disorder, dyspepsia, gastric hyperacidity and Zollinger-Ellison syndrome, comprising administering to said warm-blooded animal a pharmaceutically effective anti-ulcerative amount of an optically active pyrrolopyridazine compound or a pharmaceutically acceptable salt thereof as claimed in claim 1.

23. The method according to claim 22, wherein the warm-blooded animal is a human.

24. The method according to claim 23, wherein the method is for the treatment of said ulcerative disease.

25. A method for the treatment or prevention of *Heliobacter pylori* infection in a human comprising administering to said human a pharmaceutically effective anti-*Heliobacter pylori* amount of an optically active pyrrolopyridazine compound or a pharmaceutically acceptable salt thereof as claimed in any one of claims 1 to 18.

26. A process for synthesizing an optically active pyrrolopyridazine compound of formula (I) or a pharmaceutically acceptable salt thereof:

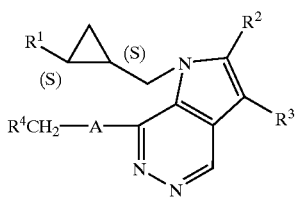

(I)

wherein $R^1$, $R^2$, $R^3$, $R^4$ and A are as defined below, which comprises reacting an optically active halogenopyrrolopyridazine compound of the formula (VI):

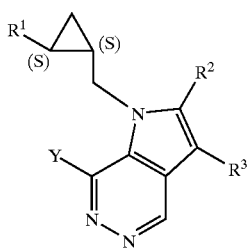

(IV)

wherein $R^1$ is a $C_1$–$C_6$ alkyl group; $R^2$ and $R^3$ are each independently a $C_1$–$C_6$ alkyl group; and Y is a halogen atom with a compound of the formula (VII):

R⁴CH₂—A—H (VII)

wherein $R^4$ is a $C_6$–$C_{10}$ aryl group which is unsubstituted or substituted with one or more substituents selected from the group consisting of $C_1$–$C_6$ alkyl, halogeno $C_1$–$C_6$ alkyl, $C_1$–$C_6$ alkoxy, halogeno $C_1$–$C_6$ alkoxy and halogen; and A is an imino group, an oxygen atom or a sulfur atom.

27. A process for synthesizing an optically active pyrrolopyridazine compound of the formula (I) or a pharmaceutically acceptable salt thereof:

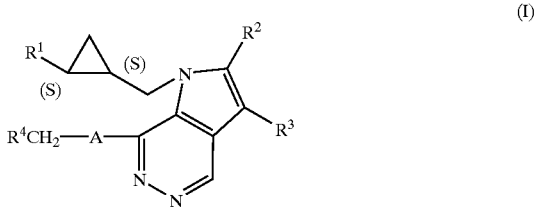

(I)

wherein $R^1$, $R^2$, $R^3$, $R^4$ and A are as defined below, which comprises (a) reacting a racemic halogenopyrrolopyridazine compound of the formula (VIa):

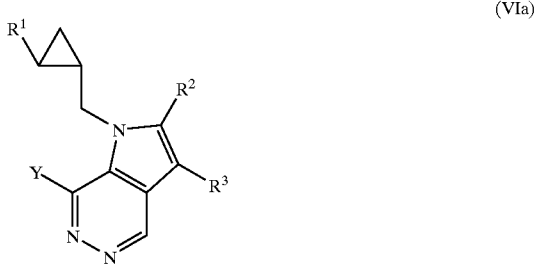

(VIa)

wherein $R^1$ is a $C_1$–$C_6$ alkyl group; $R^2$ and $R^3$ are each independently a $C_1$–$C_6$ alkyl group; and Y is a halogen atom with a compound of the formula (VII):

R⁴CH₂—A—H (VII)

wherein $R^4$ is a $C_6$–$C_{10}$ aryl group which is unsubstituted or substituted with one or more substituents selected from the group consisting of $C_1$–$C_6$ alkyl, $C_1$–$C_6$ halogeno alkyl, $C_1$–$C_6$ alkoxy, $C_1$–$C_6$ halogeno alkoxy and halogen; and A is an imino group, an oxygen atom or a sulfur atom; and (b) carrying out an optical resolution of the racemic product from step (a).

* * * * *

UNITED STATES PATENT AND TRADEMARK OFFICE
CERTIFICATE OF CORRECTION

PATENT NO. : 6,670,360 B2 Page 1 of 1
DATED : December 30, 2003
INVENTOR(S) : Hagihara et al.

It is certified that error appears in the above-identified patent and that said Letters Patent is hereby corrected as shown below:

<u>Column 19,</u>
Line 29, delete "(IV)" and insert -- (VI) --.

Signed and Sealed this

Twenty-sixth Day of July, 2005

JON W. DUDAS
*Director of the United States Patent and Trademark Office*